US00PP17187P2

(12) United States Plant Patent
Danziger

(10) Patent No.: US PP17,187 P2
(45) Date of Patent: Nov. 7, 2006

(54) ***TORENIA* PLANT NAMED 'DANTOHONEYMON'**

(50) Latin Name: ***Torenia* sp.**
Varietal Denomination: Dantohoneymon

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/144,631

(22) Filed: Jun. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited
U.S. PATENT DOCUMENTS

PP14,302 P2 * 11/2003 Miyazaki ..... Plt./263

OTHER PUBLICATIONS http://www.cpvo.eu.int/module_tech/pending_applications.php?SPECIEID=TORE1.*

* cited by examiner

*Primary Examiner*—Wendy Haas
(74) *Attorney, Agent, or Firm*—Foley & Lardner LLP

(57) ABSTRACT

A new and distinct *Torenia* plant named 'Dantohoneymon' characterized by having shiny green foliage, doted with plenty of delicate, funnel form, cup shaped flowers in shades of pale red-purple and pink; vigorous, bush, cascading, rounded and compact growth habit; densely branched plant habit which gracefully cascades from hanging baskets; early flowering response and stays in full bloom in moderate climate; suitable for use as an annual for hanging pots outdoors under partial shade; and good weather tolerance with preferred temperature range of 15 to 25° C.

2 Drawing Sheets

Botanical designation: *Torenia* sp.
Variety denomination: 'Dantohoneymon'.

BACKGROUND OF THE INVENTION

The present invention relates to a new and distinct cultivar of *Torenia* plant of the Scrophulariaceae family, hereinafter referred to by the cultivar name 'Dantohoneymon'.

The new cultivar was originated in a planned mutant selection and monitoring program in Moshav Mishmar Hashiva Israel. 'Dantohoneymon' was discovered and selected by the inventor, Gabriel Danziger, in November of 2002 as an induced shoot mutation on a single flowering plant of the *Torenia* cultivar designated 'TR-1-2212' (unpatented), grown in a controlled, cultivated environment in Moshav Mishmar Hashiva, Israel.

'Dantohoneymon' is an induced mutant of the cultivar *Torenia* 'TR-1-2212'. The mutation arose by radiation, as a side shoot, stabilized by removing the cutting from the mutated sector of the treated plant.

Asexual reproduction of the new cultivar by soft tip cuttings was first performed in November of 2002 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The follwing traits have been repeatedly observed and are determined to be unique characteristics of 'Dantohoneymon' which in combination distinguish this *Torenia* as a new and distinct cultivar:

1. Shiny green foliage, doted with plenty of delicate, funnel form, cup shaped flowers in shades of pale red-purple and pink;
2. Vigorous, bush, cascading, rounded and compact growth habit;
3. Densely branched plant, gracefully cascading from hanging baskets;
4. Early flowering and stays in full bloom in moderate climate;
5. Suitable for use as an annual for hanging pots outdoors under partial shade.
6. Good weather tolerance with preferred temperature range of 15° C. to 25° C.

Of the many commercial cultivars known to the present inventor, the most similar in comparison to the new *Torenia* cultivar 'Dantohoneymon' is the *Torenia* cultivar designated 'TR-1-2212' (unpatented) in the following characteristics described in Table 1:

TABLE 1

| Character | 'Dantohoneymon' | 'TR-1-2212' |
|---|---|---|
| Flower color | Pale Red-Purple and Pink | Pink and Violet |
| Flower size (cm) | Length: 3 cm<br>Width: 3 cm | Length: 3.8 cm<br>Width: 3 cm |
| Growth habit | Bush, cascading | Bush, cascading |
| Flowering time | 9 weeks from planting | 10 weeks from planting |

BRIEF DESCRIPTION OF THE DRAWINGS

The accompanying photographic drawings illustrate the overall appearance of the new *Torenia* cultivar 'Dantohoneymon' showing the colors as true as is reasonably possible with colored reproductions of this type. Colors in the photographs may differ slightly from the color values cited in the detailed botanical description which accurately describe the color of 'Dantohoneymon'.

The first photograph shows a side perspective view of a typical flowering plant of 'Dantohoneymon' in a hanging planter at 3 months of age.

The second photograph shows a close-up view of the typical flowers, buds and leaves of 'Dantohoneymon' at 3 months of age.

DETAILED BOTANICAL DESCRIPTION

The new *Torenia* cultivar 'Dantohoneymon' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of the new cultivar 'Dantohoneymon' as grown in a greenhouse in Moshav Mishmar Hashiva, Israel, under conditions which closely approximate those generally used in commercial practice. For use as a pot plant, plants of 'Dantohoneymon' are grown outdoors in a moderate climate and grown indoors during the winter. Irrigation and fertilization are needed on a regular basis. Plant of 'Dantohoneymon' are usually grown in full sunlight, but partial shade is requird in mid-summer. Plants of 'Dantohoneymon' are fully grown in 3 months from planting a cutting in the summer season and bloom all year-round in a moderate climate.

Color references are made to The Royal Horticultural Society Colour Chart (R.H.S.), 2001 edition, except where general colors of ordinary significance are used. Color values were taken under daylight conditions at approximately 12:00 noon in June of 2004 in Moshav Mishmar Hashiva, Israel. The age of the plant described is 3 months.

Classification:
- *Botanical.*—*Torenia* sp.
- *Commercial.*—Honey Moon.

Parentage:
- *Parent.*—Induced shoot mutation of *Torenia* cultivar 'TR-1-2212' (unpatented).

Propagation: Tissue culture (micropropagation of young *in vitro* plantlet) and soft tip cuttings.

Plant:
- *Form.*—Bush, cascading.
- *Growth habit.*—Rounded and compact.
- *Height.*—15 to 24 cm.
- *Spread.*—About 50 cm.
- *Blooming period.*—All year round in moderate climate.
- *Cold tolerance.*—Frost tender. Temperature below 5° C. may damage plants.
- *Vigor.*—Plants are fully grown in 3 months from planting a cutting in summer.

Stem:
- *Color.*—Yellow-Green, RHS 144-A.
- *Length.*—25 cm maximum length.
- *Diameter.*—About 0.3 cm.
- *Pubescence.*—Minimal and sporadic; stem is quadrangular, few hairs on the edges.
- *Branching.*—About 5 to 9 main branches from the base that split into secondary and tertiary branches.
- *Length of internodes.*—3.8 to 5 cm.

Foliage:
- *Overall shape.*—Convex, deltoid.
- *Apex.*—Reniform.
- *Base.*—Cordate.
- *Size of leaf.*—Length: About 4.3 cm. Width: About 3.3 cm.
- *Margin.*—Serrate.
- *Color.*—Center color of leaf: Yellow-Green, RHS 146-A. Upper side: Yellow-Green, RHS 146-A. Under side: Yellow-Green, RHS 146-B.
- *Leaf texture.*—Pubescent.
- *Venation.*—Not prominent.
- *Petioles.*—Length: 1.0 to 1.3 cm. Diameter: About 0.2 cm. Color: Yellow-Green, RHS 146-B.

Flowers:
- *Blooming period.*—All year round in moderate climate.
- *Flowering stem.*—Flowers appear along the growing stems; commonly 3 to 8 on the end of each grown stem.
- *Flowering longevity.*—About 4 to 7 days on the plant, depending on temperature.
- *Type.*—Single.
- *Shape.*—Funnel form.
- *Orientation at opening.*—Slanted upward.
- *Fragrance.*—None.
- *Flower length.*—About 3 cm.
- *Flower width.*—About 3 cm.
- *Bud.*—Shape: Oblong, cylindrical, ellipsoidal, 5 winged. Size: Length: About 1.5 cm. Diameter: About 0.7 cm. Color: Mixture of purple-violet shades, RHS N80B and RHS 81A. Texture: Pubescence on winged edges.
- *Floral tube.*—Length: About 3.5 cm. Color: Outside: Mixture of purple shades, RHS 76A, RHS 76B and RHS N78D. Inside: Purple, RHS 76A, and yellow-orange, RHS 14A.
- *Petals.*—Number: Four, fused to floral tube. Length: Upper: About 2.5 cm. Sides: About 2 cm. Lower: About 2 cm. Width: Upper: About 1.5 cm. Sides: About 1.2 cm. Lower: About 1.7 cm. Shape: Corolla tube cylindrical or often broadened above, 2-lipped, the upper lip faintly 2-lobed, the lower lip 3-lobed. Apex: Rounded. Base: Fused. Margin: Undulated. Color: The upper lip pale purple with purple corolla, lower and side lips red-purple, yellow blotch in middle of lower lip. Mature: Upper Side: A mixture of red-purple, RHS 72B (side lips); purple, RHS 76B (center and upper lips); orange, RHS 24A; purple, RHS 75A (margin) and yellow, RHS 7A (yellow dot). Under Side: A mixture of purple, RHS 77C (upper lip) and RHS 75A.(side lips). Margin: A mixture of red-purple, RHS72B and purple, RHS 75A. Throat: A mixture of purple, RHS 76B (upper throat) and orange, RHS 24A (lower throat). Immature: Upper Side: A mixture of purple, RHS N78A (side lips); yellow, RHS 7A (yellow dot); purple, RHS 76A(center and upper lips) and purple-violet, RHS N80C (lower throat). Under Side: A mixture of purple-violet, RHS N80B (lips) and RHS N80C (throat). Margin: Purple, RHS N78A. Throat: Purple-violet, RHS N80C.
- *Sepals.*—Number: 5. Length: About 1.7 cm. Width: Abut 0.4 cm. Shape: Two-lobed, 5 winged. Apex: Acute. Base: Wedge shaped. Margin: Undulated. Color: Yellow-green, RHS 144-A.
- *Peduncle.*—Length: About 1.4 cm. Diameter: About 0.2 cm. Texture: Smooth. Color: Yellow-Green, RHS 144-A.

Reproductive organs:

*Androecium.*—Stamen: Number: 2 pairs per flower; fused. Color: Purple, RHS 76 D. Anther: Length: About 0.4 cm; upper anthers are shorter — about 0.3 cm. Width: About 0.05 cm. Color: Purple, RHS 76 D. Spur: Present. Filament: Length: About 1.4 cm; lower filaments are shorter — about 0.3 cm. Width: About 0.05 cm. Color: Purple, RHS 76 D. Pollen: Amount: Sparse amount. Color: White, RHS N155C. Requirements for pollination: Young flowers, vital pollen, and receptive, open stigma.

*Gynoecium.*—Pistil: Number: One per flower. Length: About 2.1 cm. Stigma: Shape: Two lobes, open to opposite sides, deltoid shape. Length: About 0.25 cm. Width: About 0.3 cm. Color: Purple, RHS 76B. Style: Length: About 1.7 cm. Color: Purple, RHS 76C. Ovary: Number: 1. Length: About 0.5 cm. Width: About 0.25 cm. Color: Green, RHS 143-A.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'Dantohoneymon', substantially as illustrated and described herein.

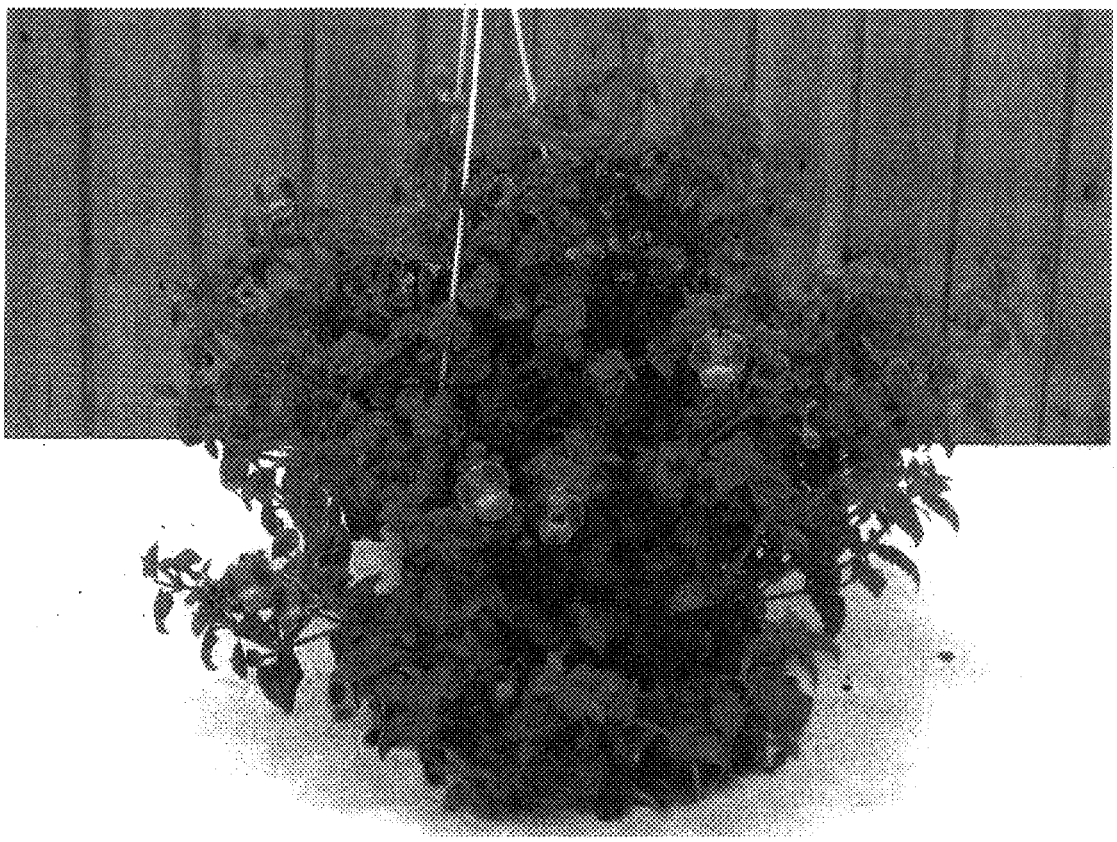

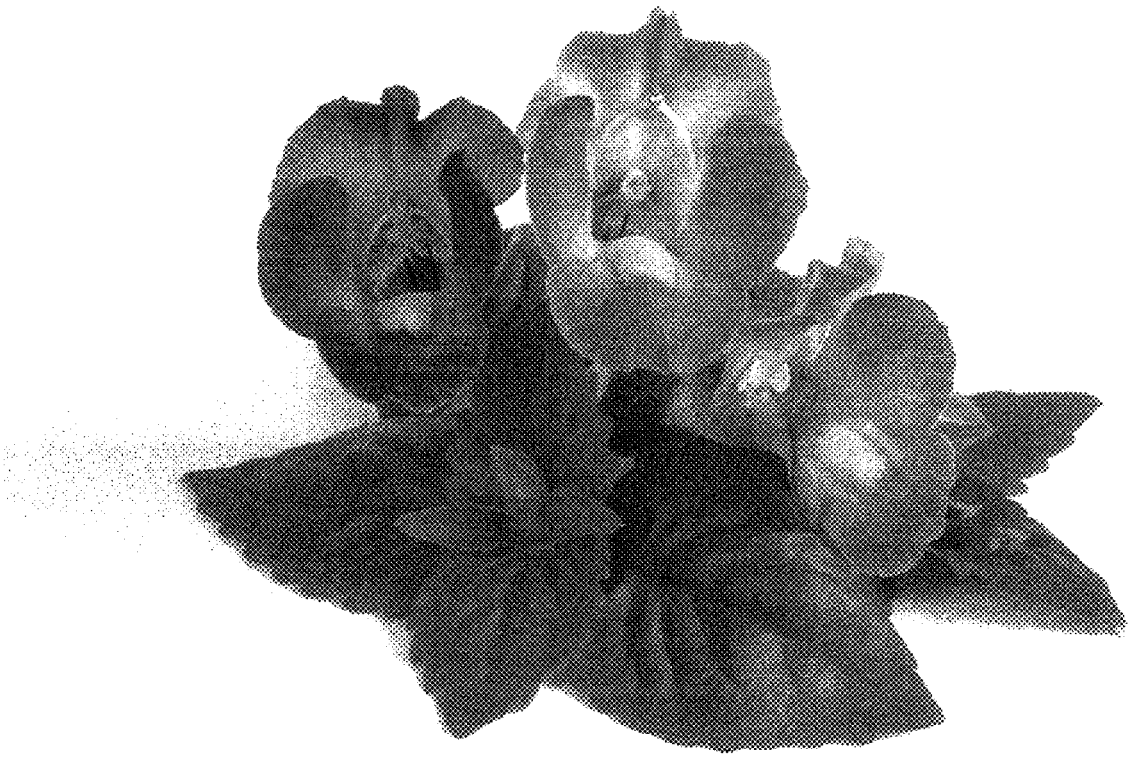

* * * * *